United States Patent
Mietke

(10) Patent No.: US 10,304,566 B2
(45) Date of Patent: May 28, 2019

(54) METHOD AND SYSTEM FOR CONTROL OF ELECTROMECHANICAL MEDICAL DEVICES

(71) Applicant: SAP SE, Walldorf (DE)

(72) Inventor: Sebastian Mietke, Walldorf (DE)

(73) Assignee: SAP SE, Walldorf (DE)

( * ) Notice: Subject to any disclaimer, the term of this patent is extended or adjusted under 35 U.S.C. 154(b) by 355 days.

(21) Appl. No.: 15/247,962

(22) Filed: Aug. 26, 2016

(65) Prior Publication Data

US 2018/0060514 A1    Mar. 1, 2018

(51) Int. Cl.
| | | |
|---|---|---|
| *G05D 23/00* | (2006.01) | |
| *G16H 40/63* | (2018.01) | |
| *G05B 15/02* | (2006.01) | |
| *G06F 19/00* | (2018.01) | |

(52) U.S. Cl.
CPC ............ *G16H 40/63* (2018.01); *G05B 15/02* (2013.01); *G06F 19/00* (2013.01)

(58) Field of Classification Search
CPC .. G06F 19/00; G06F 19/3418; G06F 19/3462; G06F 19/3468; G06F 21/305; G06F 2221/2111; G16H 20/13; G16H 20/17; G16H 40/20; G16H 40/63; G16H 40/67
See application file for complete search history.

(56) References Cited

U.S. PATENT DOCUMENTS

| | | | |
|---|---|---|---|
| 6,249,705 B1 | 6/2001 | Snell | |
| 2009/0099867 A1 | 4/2009 | Newman | |
| 2013/0312066 A1* | 11/2013 | Suarez | ................ G06F 19/3418 726/4 |

FOREIGN PATENT DOCUMENTS

WO    WO-03/017061 A2    2/2003

OTHER PUBLICATIONS

Office Action for corresponding European Application No. 16185965.7 dated Jun. 14, 2018.
Search Report for corresponding European Application No. 16185965.7 dated Mar. 1, 2017.

* cited by examiner

*Primary Examiner* — Robert G Bachner
(74) *Attorney, Agent, or Firm* — Harness, Dickey & Pierce, P.L.C.

(57) ABSTRACT

A control system, a control method, and a computer readable medium having stored thereon a computer executable program code for controlling a set of electromechanical medical devices records is disclosed herein. The method comprises: receiving by a control system an instruction to be executed by an electromechanical medical device of the set; translating the received instruction into a batch of commands parsable by an electronic controller of the electromechanical device; and sending the batch of commands from the control system to the electromechanical medical device.

17 Claims, 3 Drawing Sheets

METHOD AND SYSTEM FOR CONTROL OF ELECTROMECHANICAL MEDICAL DEVICES

TECHNICAL FIELD

This invention relates to electronic systems for controlling electromechanical medical devices. In particular, this invention relates to a failure free operation of the electromechanical medical devices.

BACKGROUND

A lot of medical electromechanical devices are equipped with electronic controllers for controlling of their operation. Not only complex medical tools like magnetic resonance imaging or various X-Ray systems but simple ones like syringes are equipped with numerous electronic controllers of different types. Computerization of medical tools enables integrating them in computer networks and executing remote operation of them by external host computer systems. As a result the host computer systems have to be equipped with different input-output (I/O) ports supporting various computer network protocols for communication with different medical tools. In addition the host computer systems have to communicate with the medical tools using different commands. This diversity of commands, protocols, data types, etc. can make programming and/or configuring of the host computer systems very difficult. Moreover the host computer systems have to provide failure free operation of the medical tools, since this aspect is of particular importance in the healthcare sector.

SUMMARY

The disclosure generally describes a control method for controlling a set of electromechanical medical devices, a computer-readable media storing computer executable instructions for executing the control method, and a control system for controlling a set of electromechanical medical devices. The aforementioned inventive solutions can be used for operating of a control system operable for translating of instructions generated by host computer systems into batches of commands being executable by electronic controllers providing operation of a set of electromechanical medical devices. In addition, the control system can collect functionality performance values characterizing performance of the electromechanical medical devices and/or their functionalities. The collected functionality performance values can be used for predicting potential failures of the electromechanical medical devices and/or their functionalities. As a result thereof the reliability of functioning of the electromechanical medical devices can be improved.

It is an objective of embodiments of the invention to provide for a control system configured to provide effective operation of the electromechanical medical devices, a control method for performing same, and a computer readable medium having stored thereon a computer executable program code for executing the control method.

According to one embodiment, the present invention relates to a control system for controlling method for controlling a set of electromechanical medical devices. The control system comprises a computer processor and a memory storing instructions of a computer executable code which execution by the computer processor causes the control system to perform the following: receiving an instruction to be executed by an electromechanical medical device of the set; translating the received instruction into a batch of commands parsable by an electronic controller of the electromechanical device; and sending the batch of commands to the electromechanical medical device.

According to another embodiment, the present invention relates to a control method for controlling a set of electromechanical medical devices. The method comprises the following: receiving by a control system an instruction to be executed by an electromechanical medical device of the set; translating the received instruction into a batch of commands parsable by an electronic controller of the electromechanical device; and sending the batch of commands from the control system to the electromechanical medical device.

According to another embodiment, the present invention relates to a computer readable medium having stored thereon a computer executable code for execution by a computer processor controlling a control system, wherein execution of the instructions of the executable code causes the computer processor to execute the control method of the aforementioned embodiment.

These embodiments can be advantageous because they can enable effective operation of the electromechanical medical devices. A host computer can be programmed to generate instructions, which can be high level instructions related to a general operation of the electromechanical medical devices and the control system can translate them in batches for commands being parsable by controllers of the electromechanical medical devices. The advantages can be illustrated on the following example. The host computer system can operate hospital facilities in conjunction with a schedule of patient treatments. The host computer can send instructions to activate an X-Ray tool in time intervals when X-Ray treatment of patients is scheduled and to put the X-Ray tool in stand-by modus for time intervals when no X-Ray treatment of patients is scheduled. The instructions generated by the host computer can be sent to the control system, which translates them in a batch of commands parsable by the electronic controller (or e.g. computer system) controlling the X-Ray system. In its own turn the electronic controller activates the X-Ray tool and puts it in stand-by modus by executing a respective batch of commands received from the control system. Another advantage of the control system is simplicity of executing updates. A vendor of the X-Ray tool can perform software and/or hardware updates resulting in changes in commands parsable by the electronic controller. After execution of such an update there is no need to update the host computer and compromise its performance related to management of the hospital facilities, because the control system can be updated such that it translates the instructions generated by the host computer system in new batches of commands parsable by electronic controller of the X-Ray tool after update executed by the vendor.

The details of one or more implementations of the subject matter of this specification are set forth in the accompanying drawings and the description below. Other features, aspects, and advantages of the subject matter will become apparent from the description, the drawings, and the claims.

DETAILED DESCRIPTION

Figure 1:
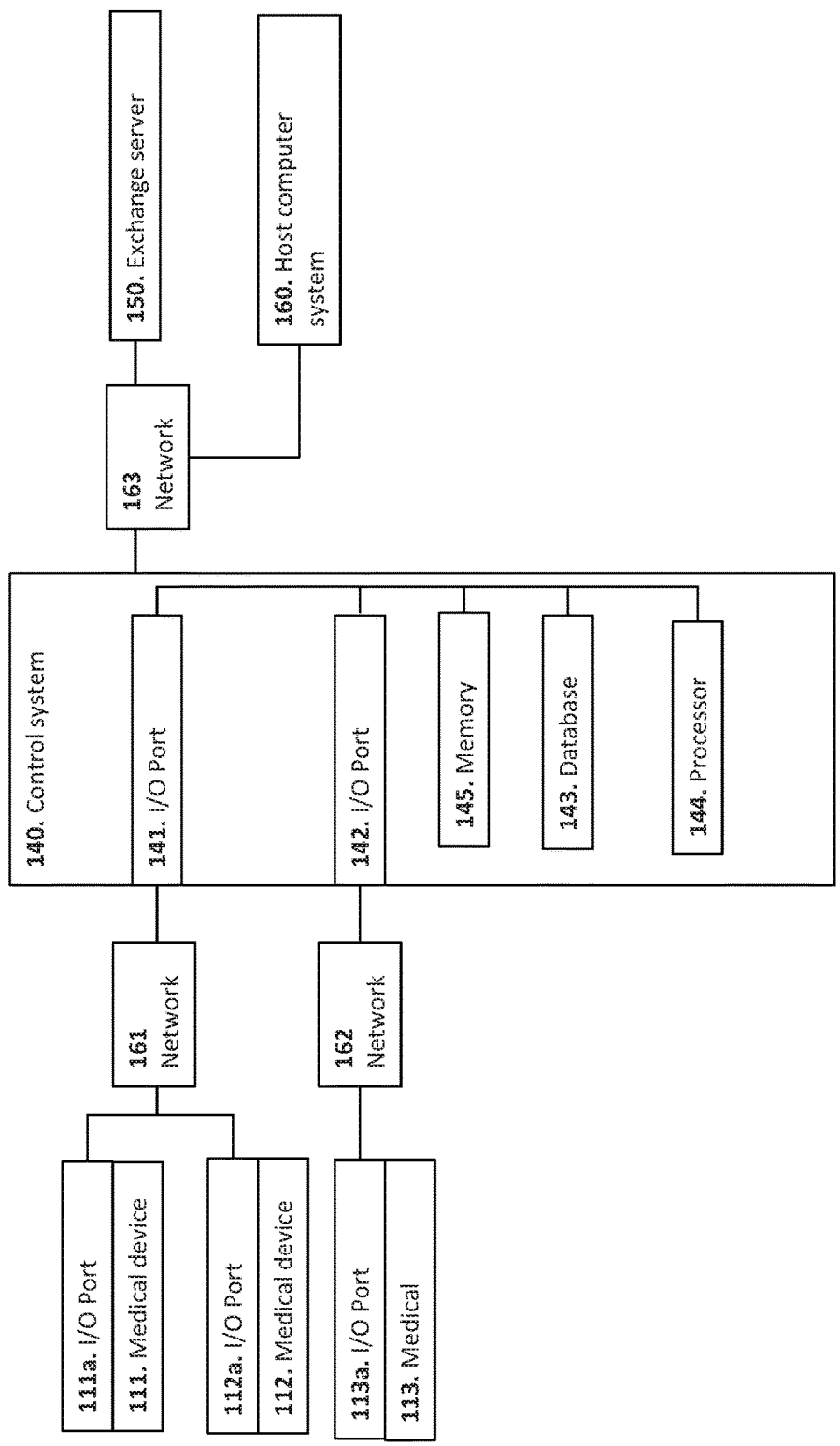
FIG. 1 is a block diagram illustrating an example environment for controlling electromechanical medical devices.

This disclosure generally describes computer-implemented methods, computer-readable media, and control systems for controlling electromechanical medical devices. The electromechanical medical device can be for instance a syringe, a perfusion tool, a magnetic resonance imaging system, an X-Ray tool, a patient monitoring system, etc. The following description is presented to enable any person skilled in the art to practice the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

According to another embodiment of the present invention, the instruction comprises an instruction specification and an identification information for identifying the electromechanical medical device. The control system comprises a database storing batches of commands parsable by electronic controllers of electromechanical medical devices of the set. Each of the batches of commands is associated with a respective instruction specification and a respective device type of an electromechanical medical device of the set. Each of the electromechanical medical devices of the set has a respective device type. The database stores technical data enabling identification of the device type of electromechanical medical device by its identification information. The database stores parameter values for entering in parameter fields of commands of the batches of commands. Each of the parameter values is associated with a respective command in the batch of commands and an identification information of a respective electromechanical medical device of the set. The translating of the received instruction into the batch of commands parsable by the electronic controller of the electromechanical medical device comprises: identifying in the database a device type associated with the identification information comprised in the instruction using the technical data; identifying in the database the batch of commands associated with the identified device type and the instruction specification comprised in the instruction; identifying in the database a parameter value associated with the identification specification and a command of the identified batch of commands; and entering the identified parameter value in a respective parameter field of the command of the identified batch of commands.

This embodiment can be advantageous, because it can provide for an effective management of the data related to translation of the instructions. The batches of commands are identified according to the device type while the parameter values to be entered in the fields of the commands are identified according to the identifications of the devices. As a result thereof there is no need to store batches of commands being specific for each of the devices.

According to another embodiment of the present invention the control method comprises: receiving the batch of commands by the electromechanical medical device; the electronic controller causing the electro-mechanical device to execute the batch of commands; the electronic controller registering performance data related to the execution of the batch of commands; sending the performance data from the electromechanical medical device to the control system; and receiving the performance data by the control system.

This embodiment can be advantageous, because it can provide for an advanced failure free operation of the electromechanical devices. The control system receives the performance data related to execution of the batches of commands. In this case the control system can evaluate the received data in order to ensure correctness of execution of the batches of commands.

According to another embodiment, the performance data comprises an indicator value. Compliance of the indicator value with its specification indicates that the batch of commands is executed successfully on the electromechanical medical device. The control method comprises the following: receiving by the control system another instruction to be executed by the electromechanical medical device of the set; translating the another received instruction into another batch of commands parsable by the electronic controller of the electromechanical device; and performing the following if the indicator value comprised in the performance data received by the control system complies with its specification: sending the another batch of commands from the control system to the electromechanical medical; receiving the another batch of commands by the electromechanical medical device; the electronic controller causing the electromechanical device to execute the another batch of commands; the electronic controller registering another performance data related to the execution of the another batch of commands; sending the another performance data from the electromechanical medical device to the control system; and receiving the another performance data by the control system.

This embodiment can be advantageous, because it can provide for correctness of execution of batches of commands. For instance one of the batches of commands can be executed on the electromechanical medical device only when execution of another one of the batches of commands is completed on the same electromechanical medical device.

According to another embodiment of the present invention, the control system comprises a database storing rules determining sequence of execution of batches of commands. The control method comprises: receiving by the control system another instruction to be executed by another electromechanical medical device of the set; translating the another received instruction into another batch of commands parsable by another electronic controller of the another electromechanical device; sending the another batch of commands from the control system to the another electromechanical medical device, wherein the sending of the another batch of commands from the control system to the another electromechanical medical device is executed after the receiving of the performance data by the control system if according to one of the rules the batch of commands has to be executed before the another batch of commands; receiving the another batch of commands by the another electromechanical medical device; and the another electronic controller causing the another electromechanical device to execute the another batch of commands.

This embodiment can be advantageous, because it can provide for correctness of execution of batches of commands on different electromechanical medical devices. For instance, one of the batches of commands can be executed on the electromechanical medical device only when execution of another one of the batches of commands is completed on another electromechanical medical device.

According to another embodiment of the present invention, the control method comprises the control system reporting a failure of the electro-mechanical device when a value of a time interval between the sending of the batch of commands from the control system to the electromechanical medical device and the receiving of the performance data by the control system is bigger than a predefined value.

This embodiment can be advantageous because it can provide a simple detection of failure of the electromechanical medical device. The absence or a delay of the response from the electromechanical medical device can be an indicative of its failure. The delay can indicate that software of the electronic controller has an error, e.g. accumulation of errors.

According to another embodiment of the present invention, each electromechanical medical device has a respective device type. The instruction comprises an instruction specification and an identification information for identifying the electromechanical medical device. The control system comprises a database storing batches of commands parsable by electronic controllers of electromechanical medical devices of the set. Each batch of commands stored in the database is associated with a respective instruction specification and a respective device type of an electromechanical medical device of the set. The database stores technical data enabling identification of the device type of electromechanical medical device by its identification information. An exchange server communicatively coupled to the control system stores batches of commands parsable by electronic controllers of electromechanical medical devices, instruction specifications, and values of time intervals. Each batch of commands stored on the exchange server is associated with a respective device type, a respective instruction specification, and a respective value of time interval. The control method comprises: identifying in the database a device type associated with the identification information comprised in the instruction using the technical data; identifying in the database the batch of commands associated with the identified device type and the instruction specification comprised in the instruction, wherein the identified batch of commands is the one which is executed in the step of the electronic controller causing the electro-mechanical device to execute the batch of commands; the control system sending to the exchange server the identified device type, the instruction specification comprised in the instruction, the identified batch of commands, the predefined value, and the value of the time interval between the sending of the batch of commands from the control system to the electromechanical medical device and the receiving of the performance data by the control system; the exchange server stores the identified batch of commands in association with the identified device type, the instruction specification comprised in the instruction, and the value of the time interval between the sending of the batch of commands from the control system to the electromechanical medical device and the receiving of the performance data by the control system; and the control system receiving from the exchange server the batch of commands stored on the server if the value of the time interval between the sending of the batch of commands from the control system to the electromechanical medical device and the receiving of the performance data by the control system is bigger than the predefined value and the batch of commands stored on the server is associated with the identified device type, the instruction specification comprised in the instruction, and the value of time interval being equal or less than the value of the time interval between the sending of the batch of commands from the control system to the electromechanical medical device and the receiving of the performance data by the control system.

This embodiment can be advantageous, because it can provide for an effective method of optimization of the batches of commands. Electromechanical medical devices of the same type can be installed in different hospitals. Different control systems can exchange the batches of commands for the same types of the electromechanical devices via the exchange server.

According to another embodiment of the present invention, the performance data comprises a functionality performance value characterizing performance of a functionality of the electromechanical medical device. The functionality performance value is registered when the functionality is activated in a process of the execution of the batch of commands by the electromechanical medical device. The control method comprises the control system reporting a failure of the functionality when the functionality performance value does not comply with a specification.

This embodiment can be advantageous because, it can provide for advanced monitoring of failures by the control system.

According to another embodiment of the present invention, each electromechanical medical device has a respective device type. The performance data comprises a functionality performance value characterizing performance of a functionality of the electromechanical medical device. The functionality performance value is registered when the functionality is activated in a process of the execution of the batch of commands by the electromechanical medical device. The instruction comprises an instruction specification and an identification information for identifying the electromechanical medical device. The control system comprises a database storing batches of commands parsable by electronic controllers of electromechanical medical devices of the set. Each of the batches of commands stored in the database is associated with a respective instruction specification and a respective device type of an electromechanical medical device of the set. The database stores technical data enabling identification of the device type of electromechanical medical device by its identification information. An exchange server communicatively coupled to the control system stores batches of commands parsable by electronic controllers of electromechanical medical devices, instruction specifications, and functionality performance values characterizing performance of functionalities of electromechanical medical devices. Each of the batches of commands stored on the server is associated with a respective device type, a respective instruction specification, and at least one respective functionality performance value. The control method comprises: identifying in the database a device type associated with the identification information comprised in the instruction using the technical data; identifying in the database the batch of commands associated with the identified device type and the instruction specification description comprised in the instruction, wherein the identified batch of commands is the one which is executed in the step of the electronic controller causing the electro-mechanical device to execute the batch of commands, the control system sending to the exchange server the identified device type, the instruction specification comprised in the instruction, the identified batch of commands, the specification, and the functionality performance value characterizing performance of the functionality which is activated in the process of the execution of the batch of commands by the electromechanical medical device; and the exchange server storing the identified batch of commands in association with the identified device type, the instruction specification comprised in the instruction, and the functionality performance value characterizing performance of the functionality which is activated in the process of the execution of the batch of commands by the electromechanical medical device; the control system receiving from the exchange server the batch of commands stored on the server if the functionality performance value characterizing performance of the functionality which is activated in the process of the execution of the batch of commands by the electromechanical medical device does not comply with the specification and the batch of commands stored on the server is associated with the identified device type, the instruction specification comprised in the instruction and the functionality performance value complying with the specification.

This embodiment can be advantageous because, different control systems can exchange via the exchange server different batches of commands and functionality performance values generated in processes of execution of the batches. This exchange can facilitate development of optimized batches of commands.

According to another embodiment of the present invention, the performance data comprises a functionality performance value characterizing performance of a functionality of the electromechanical medical device. The functionality performance value is registered when the functionality is activated in a process of the execution of the batch of commands by the electromechanical medical device. The control system comprises a database configured to store performance trend data related to the performance of the functionality. The control method comprises: storing in the database the functionality performance value assigned to the performance trend data; and deriving failure conditions of the functionality on a basis of a comparison of the performance trend data with reference trend data, the failure conditions specifying conditions when a probability of occurrence of a failure of the functionality in a process of execution of further batches of commands by the electromechanical medical device is above a predefined value.

This embodiment can be advantageous because, it can provide for decrease in failures of the electromechanical medical devices during execution of the batches of commands. Maintenance of the electromechanical medical devices can be performed in a proactive way on a basis of failure conditions specifying conditions when the probability of failure of a functionality is above a predefined value.

According to another embodiment of the present invention, each of the electromechanical medical devices of the set has a respective device type. The database comprises a list of service applications. In the database each of the service applications in the list is associated with the respective device type of the electromechanical medical device. The instruction comprises an identification information for identifying the electromechanical medical device. The database stores technical data enabling identification of the device type of electromechanical medical device by its identification information. The control method comprises: identifying in the database a device type associated with the identification information comprised in the instruction using the technical data; identifying a service application in the list, wherein the identified service application is associated with the identified device type; and sending an alert message to the identified application, the alert message comprising the failure conditions, the identified device type, and the identification information.

This embodiment can be advantageous because, it can provide for an automated proactive servicing of the electromechanical medical devices, i.e. before the risk of failure becomes unacceptable.

According to another embodiment of the present invention, the reference trend data comprises functionality performance values characterizing performance of one or more functionalities of one or more other electromechanical medical devices.

This embodiment can be advantageous, because it can provide for a simple way of determining probability of failure. For instance the reference trend data can be performance trend data collected for electromechanical medical devices of particular type. The trend data can indicate a number of operation cycles (e.g. opening and closing of a valve) executed by each of the electromechanical devices before failure.

According to another embodiment of the present invention, at least one of the one or more electromechanical devices is not comprised in the set. The control method comprises: the control system receiving from an exchange server functionality performance values characterizing performance of one or more functionalities of the at least one of the one or more electromechanical devices.

This embodiment can be advantageous because it can provide for exchange of information related to failure of the electromechanical medical devices via the exchange server. This can be of particular advantage when only one electromechanical medical device of particular type is operated by the control system. According to another embodiment of the present invention, the set of matching criteria determines matching between specifications of hardware resources required for execution of the tiers and specifications of the hardware resources of the set of hardware resources According to another embodiment of the present invention one or more other electromechanical medical devices are comprised in the set.

This embodiment can be advantageous because the reference trend data is collected using electromechanical medical devices of the set operated by the control system. This can be of particular advantage when failures of the electromechanical medical devices depend on environment (e.g. climate) in which they are operated.

According to another embodiment of the present invention, the receiving of the performance data is performed using an input-output port of the control system and an input-output port of the electromechanical medical device. Said input-output ports being are communicatively coupled with each other. The control system is configured to register a data transmission value characterizing a property of a data carrying signal received by the input-output port of the control system from the input-output port of the electromechanical medical device. The receiving of the performance data comprises a step of the control system registering the data transmission value in a process of the receiving of the performance data. The control system comprises a database configured to store trend data characterizing properties of the data carrying signal. The control method comprises: storing in the database the data transmission value assigned to the trend data; and deriving failure conditions of the electromechanical medical device on a basis of comparison of the trend data with reference trend data, the failure conditions specifying conditions when a probability of occurrence of a failure of the electromechanical medical device in a process of execution of further batches of commands by the electromechanical medical device is above a predefined value This embodiment can be advantageous because it provides for an indirect detection of failures of the electromechanical medical devices. The quality of the signal transmitted by the input-output port of the electromechanical medical device can indicate it state and it can be used for prediction of its failure.

According to another embodiment of the present invention, the data transmission value is an amplitude of the data carrying signal.

This embodiment can be advantageous because it can provide for an effective way of detecting a failure of the electromechanical medical device. Decrease in the amplitude of the data carrying signal can indicate a degradation of a power supply of the electromechanical medical device or its input-output port.

According to another embodiment of the present invention, the data transmission value is a frequency of the data carrying signal.

This embodiment can be advantageous because it can provide for an effective way of detecting a failure of the electromechanical medical device. Changes in the frequency of the data carrying signal can indicate a degradation of an I/O port of the electromechanical medical device.

FIG. 1 illustrates an example environment for controlling a set of electromechanical medical devices 111, 112, 113, wherein each of the electromechanical medical devices 111-113 of the set can have a respective type (e.g. syringe type "XYZ"). Each of the electromechanical medical devices 111-113 can have an assigned identification information for identifying of the each electromechanical medical device (e.g. internet protocol, IP, address). Specifically, the illustrated environment includes a control system 140. The control system 140 can comprise the following components: one or more I/O ports 141, 142, a database 143, a computer processor 144 controlling the control system 140, a memory 145, and one or more data buses providing communicative coupling of the components. The I/O port 141 is communicatively coupled to an I/O port 111a of the electromechanical medical device 111 via computer network 161. The I/O port 141 is communicatively coupled to an I/O port 112a of the electromechanical medical device 112 via computer network 161. The I/O port 142 is communicatively coupled to an I/O port 113a of the electromechanical medical device 113 via computer network 162. The network 161 can be a wired network e.g. Ethernet or a wireless network e.g. WiFi. The network 162 can be a wired or a wireless network. The control system can be connected to an exchange server 150 and/or a host computer system 160 via a computer network 163. At least two of the networks 161-163 can be the same computer network. The database 143 can store batches of commands parsable by electronic controllers of electromechanical medical devices of the set, and/or technical data enabling identification of the device type of electromechanical medical device by its identification information and/or parameter values for entering in parameter fields of commands of the batches of commands. The parameter field of a command can be for instance a format of a digital value specified in the command or to be sent by a computer system executing the command. Each of the parameter values can be associated in the database with a respective command in the batch of commands and an identification information of a respective electromechanical medical device of the set. This way of data structuring can reflect different configurations of the electromechanical medical devices of the same type. For instance, two electromechanical devices of the same type can be operated using the same commands, but due to different configuration of them the format of digital values specified in the same command used for their operation can be different for these two electromechanical medical devices.

The exchange server 150 can store batches of commands parsable by electronic controllers of electromechanical medical devices. The control system 140 can send to and receive from the exchange server the batches of commands. In addition, other control systems can send to and receive from the exchange server batches of commands. The exchange server can store further information related to identification of the batches of commands and information related to their execution on the electromechanical medical devices. The control system request a substitute batch of commands to substitute currently used batch of commands when the currently used batch of commands does not comply with performance requirements. In addition vendors of the electromechanical medical tools can send to the exchange server new versions of batches of commands.

Figure 2:
FIG. 2 shows a flowchart of an example method for controlling electromechanical medical devices.

The memory 145 stores instructions of a computer executable code which execution by the computer processor 144 causes the control system 140 to perform a control method depicted on FIG. 2. The control method depicted on FIG. 2 begins with process block 200. In the process block 200 the control system receives and instruction to be executed by the electromechanical medical device. Such an instruction can be the for instance an instruction to activate an X-Ray medical tool equipped with a rotating anode X-Ray source. The activation procedure comprises pumping down a chamber of the rotating anode X-Ray source, wherein the chamber has to be evacuated first by a rotary vane vacuum pump and after the pressure in the chamber is below a predefined value if has to be further evacuated by a turbo pump. The instruction can be received via the computer network 163 from a host computer system, which can manage medical tools in a medical institution e.g. hospital. The instruction can comprise an instruction specification (e.g. activation of the X-Ray medical tool) and the identification information (e.g. Gamma Device 15) for identifying the electromechanical medical device. In case when the database 143 stores batches of commands, each of the batches of commands can be associated in the database with a respective instruction specification and a respective device type of the electromechanical medical device of the set Process block 201 is executed after process block 201. In process block 202 the control system translates the received instruction into a batch of commands parsable by an electronic controller of the electromechanical device. In the context of the aforementioned example, the batch of commands can comprise commands for activating vacuum pumps, opening/closing valves, requesting from a vacuum gauge a value of gas pressure in the chamber, etc.

Figures 3, 4:
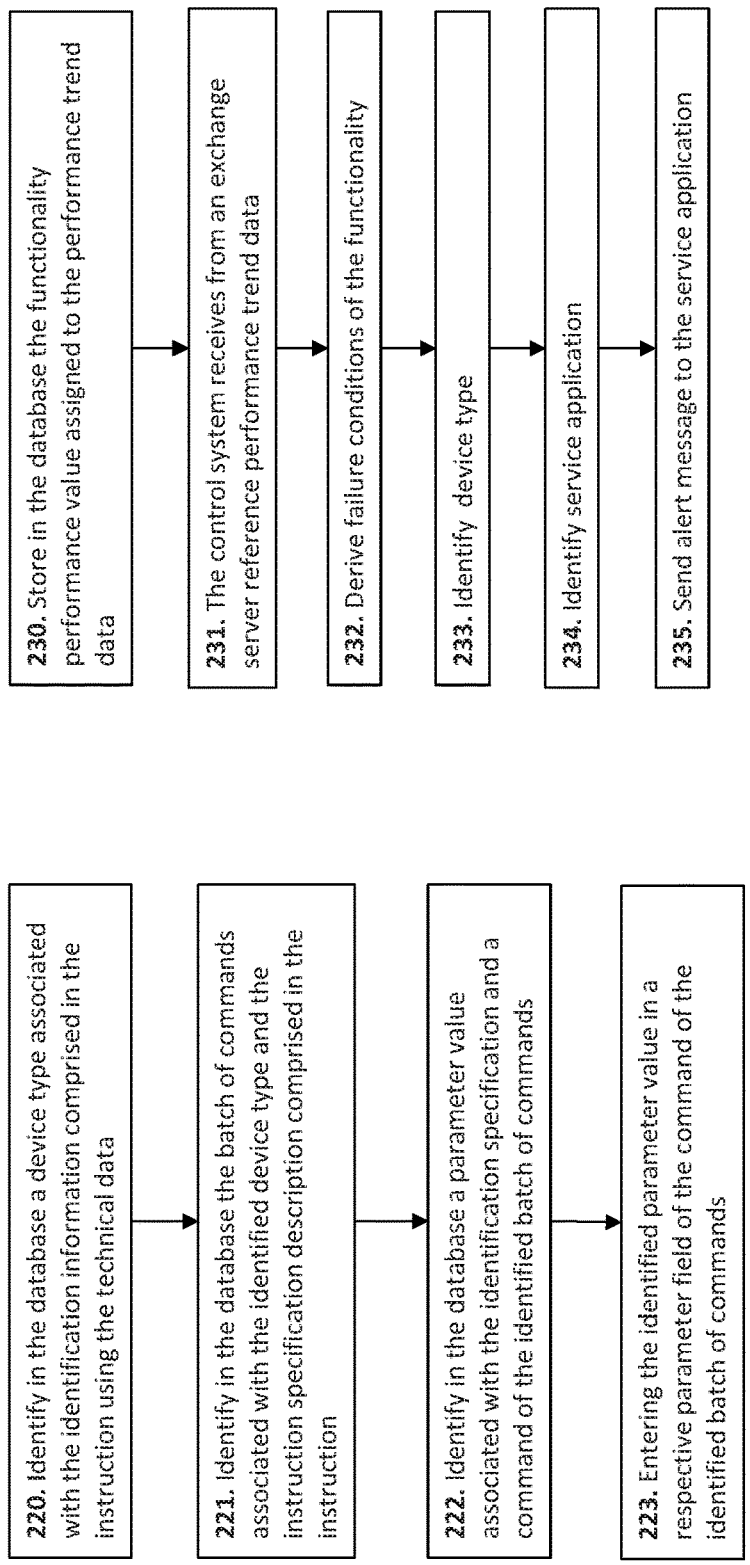
FIG. 3 shows a flowchart of an example method for controlling electromechanical medical devices.
FIG. 4 shows a flowchart of an example method for controlling electromechanical medical devices.

Process block 201 can comprise one or more process blocks depicted on FIG. 3. In process block 220 the control system 140 identifies in the database a device type associated with the identification information comprised in the instruction using the technical data stored in the database 143.

Process block 221 is executed after process block 220. In process block 221 a batch of commands associated with the identified device type and the instruction specification comprised in the instruction received in process block 200 is identified in the database. Afterwards the identified batch of commands is retrieved from the database and, if necessary, prepared by the control system for execution by an electronic controller of the electromechanical medical device which identification information is comprised in the received instruction. The preparation can be executed in the next following process blocks 222 and 223.

Process block is executed, if necessary, after process block 221. In process block a parameter value associated with the identification specification of the electromechanical medical device and a command of the identified batch of commands is identified in the database. This process block can comprise identification for each of the commands of the identified batch of commands of all parameter values associated with the identification specification of the electromechanical medical device and the each of the commands of the identified batch of commands. This process block further comprises retrieving from the database 143 the identified parameter value.

Process block 223 is executed after process block 222. In process block 223 the identified parameter value is entered in a respective parameter field of the command of the identified batch of commands. This procedure can be repeated until all identified parameter values are entered in the respective parameter fields of the commands of the identified batch of commands.

Turning back to the flowchart depicted on FIG. 2, process block 202 is executed after process block 201. In process block 202 the control system 140 sends the batch of commands to the electromechanical medical device (e.g. 111). For instance this can be done via computer network 161 by using the I/O port 141 of the control system 140 and I/O port 111a of the electromechanical medical device 111.

Process block 203 is executed after process block 202. In process block 202 the electromechanical device receives the batch of commands. Process block 204 is executed after process block 203. In process block 204 the electronic controller of the electromechanical medical device causes the electromechanical device to execute the batch of commands. Process block 205 is executed after process block 204. In process block 205 the electronic controller registers performance data related to the execution of the batch of commands. Performance data can be performance data of components of the electromechanical medical device. For instance it can be time elapsed when the valve was switched from an open state to a closed state, or it can be time elapsed when a rotor of the turbo pump was accelerating from a zero rotation speed to the nominal rotation speed. Process block 207 is executed after process block 205. In process block 207 the performance data is sent from the electromechanical medical device (e.g. 111) to the control system 140. For instance, this can be done via computer network 161 by using the I/O port 141 of the control system 140 and I/O port 111a of the electromechanical medical device 111. Process block 208 is executed after process block 207. In process block 208 the control system 140 receives the performance data from the electromechanical medical device (e.g. 111).

Process blocks 200-208 can be executed for another instruction to be executed on another electromechanical medical device or the aforementioned electromechanical medical device. Some of the batches of commands can be formulated such that process blocks 205-208 are not executed. For instance, an instruction received in process block 200 can be an instruction to lock a door though which an unauthorized person can enter a room when a medical tool (e.g. aforementioned X-Ray medical tool) is activated. The electronic controller controlling a lock of this door can be implemented such that it does not register performance data related to the batch of commands associated with the instruction to lock the door. As matter of another example, another instruction received in process block 200 could be an instruction to calibrate an X-Ray source of the aforementioned X-Ray medical tool, wherein the X-Ray source is switched on and a measured intensity of the X-Ray radiation of the X-Ray source is to be reported to the control system 140. Execution of a batch of commands associated with this instruction requires execution of process blocks 202-208. Execution of batches of commands associated with respective instructions can require execution of the batches of commands in a particular sequence, wherein execution of one batch of commands on of the electromechanical medical devices can be stated only when execution of another batch of commands on another or the same electromechanical medical device is (successfully) completed. The rules determining formations of the sequences of execution of batches of commands can be stored in the database 143. The successfulness of execution can be determined by verifying a compliance of an indicator value comprised in the performance data with its specification. Thus in case when execution of a second instruction requires a prior (successful) execution of a first instruction, process blocks 200-208 related to execution of the first instruction have to be executed before execution of process block 202 related to execution of the second instruction. An optional criterion for starting of process block 202 related to execution of the second instruction can be compliance of the indicator value received in process block 208 related to execution of the first instruction complies with its specification. When the process block 202 related to execution of the second instruction is executed the next following process blocks 203 and 204 related to execution of the second instruction are executed. Further process blocks 205-208 are executed in relation to execution of the second instruction if the batch of commands associated with the second instruction specifies execution of these process blocks.

Such sequential execution of instructions can support interlock functions for safe operation of the electromechanical medical device. Moreover for some of the electromechanical medical devices selecting specifications of indicator values in a conservative way can extend their failure free operation. For instance when a charging limit of an accumulator is set to 80-90% of its capacity it will serve longer in comparison with a case when its charging limit is set to 100%, i.e. its full capacity. The need to execute instructions in predefined sequences can be illustrated on the following example based on the aforementioned instructions to activate the X-Ray tool and to calibrate its source. The calibration of the X-Ray source cannot be started until the activation of the X-Ray tool is completed. An indicator value of activation of the X-Ray tool can be a base pressure of residual atmosphere in a vacuum chamber of the X-Ray source. Execution of both instructions require execution of process blocks 200-208. However execution of process block 202 related to execution of instruction to calibrate the X-Ray source can be started only when the indicator value received (residual pressure) by the control system in process block 208 related to execution of instruction to activate the X-Ray tool comply with its specification, i.e. the residual pressure in the chamber of the X-Ray source is low enough. Alternatively execution of process block 202 related to execution of instruction to calibrate X-Ray source can be started after execution of process block 208 related to execution of instruction to activate the X-Ray tool. In this case execution of process block 208 related to execution of instruction to activate the X-Ray tool indicates that pumping down of the vacuum chamber of the X-Ray source is successfully started. The batch of commands associated with the instruction to calibrate the X-Ray source can be received by the electronic controller of the X-Ray tool because it has an internal interlock enabling calibration of the X-Ray source only when its vacuum chamber is pumped down in accordance with internal specification. Selecting an option when execution of X-Ray source calibration is triggered by the internal interlock can save time, on the other hand setting specification of the indicator value (threshold base pressure in the vacuum chamber of the X-Ray source) lower than a threshold pressure triggering the internal interlock for enabling calibration of the X-Ray source can extend period of failure free operation of the X-Ray source.

The aforementioned sequential execution of instructions can not only support interlock functions but support overriding them. For instance, one of the batches of commands can comprise a command to switch off one or more of particular interlocks interlocks of the electromechanical medical device. After execution of this command a new interlock configuration is determined exclusively by sequence of execution of instructions. This regime can be beneficial when the electromechanical medical device is serviced or the interlock configuration is optimized.

A value of time interval between execution of the sending of the batch of commands from the control system to the electromechanical medical device in process block 202 and execution of the receiving of the performance data by the control system in process block 208 being bigger than a predefined value can indicate a failure of the electromechanical medical system. For instance it can indicate that the software executed on the electronic controller of the electromechanical medical device has an error (e.g. it so called accumulation error which increases throughout execution of the software code by the electronic controller) or it can indicate physical degradation of a particular component of the electromechanical medical device (e.g. opening or closing of a vacuum valve in the aforementioned X-Ray tool takes too long due to its degradation). In addition or as alternative it can indicate that the batch of commands has to be improved because its execution takes too long time. When a value of the time interval between execution of the sending of the batch of commands from the control system to the electromechanical medical device in process block 202 and execution of the receiving of the performance data by the control system in process block 208 is bigger than the predefined value the control system can report a failure, for instance by sending an alert message to the host computer which has sent the respective instruction to be executed on the electromechanical medical device.

The control system can report a failure of the functionality when a functionality performance value does not comply with a specification. For instance by sending another alert message to the host computer which has sent the respective instruction to be executed on the electromechanical medical device. The performance data received in process block 208 can comprise a functionality performance value characterizing performance of the functionality of the electromechanical medical device. The functionality performance value is registered when the functionality is activated in a process of the execution of the batch of commands by the electromechanical medical device in process block 204. The functionality performance value can be for instance an elapsed time interval when a mechanical component of the electromechanical medical device is moved from one position to another. The movement of the mechanical component can be performed by means of the electromechanical actuator. The performance parameter value can be for instance time elapsed in a process of opening of a vacuum valve of the aforementioned X-Ray medical tool, i.e. time needed to move a mechanical component arranged for closing a gas flow through the vacuum valve from a position in which it closes the gas flow through the vacuum valve into a position in which the gas flow through the vacuum valve in enabled. When it takes too long to open the valve it can indicate that it is damaged or one of its components is degraded. In addition or as alternative, the functionality performance value which does not comply with the specification can indicate that the batch of commands has to be improved.

As it is mentioned above the exchange server 150 can store batches of commands which can be used by the control system 140. For instance, each batch of commands stored on the exchange server can be associated with a respective device type, a respective instruction, and a respective value of a time interval. Wherein the values of the time intervals are registered as described above. Besides sending the alert message the control system can request from the exchange server another batch of commands to substitute the currently used batch of commands which execution cases sending the alert message. Alternatively, each batch of commands stored on the exchange server can be associated with a respective device type, a respective instruction specification, and at least one functionality performance value. Wherein the functionality performance values are registered as described above. The batches of commands can be stored on the exchange server in a way that the exchange server can provide an alternative batch of commands in both of the aforementioned cases. In this case, each of some of batches of commands stored on the exchange server can be associated with a respective device type, a respective instruction, and a respective value of a time interval; and each of some of the batches of commands stored on the exchange server can be associated with a respective device type, a respective instruction specification, and at least one functionality performance value. In addition the exchange server can store new and/or back-up batches of commands, each of which is associated with a respective device type and a respective instruction specification. Thus the new and back-up batches stored on the exchange server can be identified in the same way as the batches of commands stored in the database 143.

Turning back to flow chart diagram on FIG. 2, the control method can further comprise optional process blocks 209-211. In process block 208 the control system sends to the exchange server the identified device type, the instruction specification comprised in the instruction, the identified batch of commands. Further it can send the value of the time interval between the sending of the batch of commands from the control system to the electromechanical medical device and the receiving of the performance data by the control system and its specification, i.e. the predefined value. Alternatively or in addition it can send the functionality performance value characterizing performance of the functionality which is activated in the process of the execution of the batch of commands by the electromechanical medical device and its specification. Sending the batch of commands to the exchange server in a case when the batch of commands does not provide compliance with the specification can be beneficial for other applications having more broad and/or different specification windows. In other words, another control system can have specifications for execution of a batch of commands which enable utilization of a batch of commands which was previously uploaded to the exchange server, despite the fact that it did not provide compliance of said respective time interval and/or said functionality performance value with the respective specifications of the control system which uploaded said batch of commands to the exchange server.

Process block 210 is executed after process block 209. In process block 209 the exchange server receives information sent to it in process block 209. Afterwards it stores the received batch of commands in association with the identified device type and the instruction specification comprised in the instruction received in process block 200. The received batch of commands is further associated with the value of the time interval between the sending of the batch of commands from the control system to the electromechanical medical device and the receiving of the performance data by the control system if the value of the time interval is sent. The received batch of commands is further associated with the functionality performance value characterizing performance of the functionality which is activated in the process of the execution of the batch of commands by the electromechanical medical device if the functionality performance value is sent. The stored batch of commands can be sent to other control systems when it complies with requirements/specifications sent by requests of the other control systems.

Process block 211 is executed after process block 210. In process block 210 the exchange server checks whether the value of the time interval between the sending of the batch of commands from the control system to the electromechanical medical device and the receiving of the performance data by the control system complies with its specification if the value of the time interval between the sending of the batch of commands from the control system to the electromechanical medical device and the receiving of the performance data by the control system is sent to the exchange server. The exchange server further checks whether the functionality performance value characterizing performance of the functionality which is activated in the process of the execution of the batch of commands by the electromechanical medical device complies with its specification if the functionality performance value characterizing performance of the functionality which is activated in the process of the execution of the batch of commands by the electromechanical medical device complies with its specification. If at least one non-compliance is found then it executes a search in order to identify a batch of commands stored on the server which is associated with the identified device type, the instruction specification comprised in the instruction received in process block 200, a functionality performance value complying with the respective specification received in process block 209, and a value of a time interval complying with the respective specification received in process block 209. One of the latter two criteria for identification of the batch of commands can be optional, since utilization of these criteria depends on the information sent in process block 209. If the batch of commands is identified it is sent by the exchange server to the control system.

The functionality performance values can be used for prediction of failure of the functionalities. Prediction of failure requires storing the functionality performance values registered in a process of execution of several batches of commands. At least one of the executed batches can be different than the other. The database can be configured to store performance trend data related to the performance of the functionality. The performance trend data is built by collecting functionality performance values of the same functionality, e.g. time needed to close a vacuum valve of the aforementioned X-Ray system can be registered several times. If the performance trend data shows that the time needed to close the vacuum valve increases it can be an indicative of potential failure in the future. Failure conditions of the functionality can be derived by comparing the performance trend data of the functionality with reference trend data. The reference trend data can comprise performance trend data of the same or similar functionalities. For instance, it can be a failure statistics of vacuum valves showing a number of open-close cycles before failure for a plurality of the same or similar valves. The reference trend data can comprise data indicative of a probability of failure of particular functionality versus a number of times it was activated/used. In some cases the reference trend data can be a statistical distribution function of probability of failure of a particular functionality versus a number of times the functionality was activated/used. The failure conditions can specify conditions when a probability of occurrence of a failure of the functionality in a process of execution of further batches of commands by the electromechanical medical device is above a predefined value. For instance, when the reference trend data is determined by the aforementioned statistical distribution function, the performance trend data can be a counter of times the functionality is activated/used. In this case deriving of the failure conditions of the functionality of a basis of comparison of the performance trend data with the reference trend data can be a calculation of the probability of failure of the functionality by using the statistical distribution function, wherein a value of a counter is used as its argument. The reference trend data determined by the statistical distribution function can be formulated for instance as a mathematical equation or in a tabular form.

The reference trend data can comprise several performance trends of the same functionality in different electromechanical medical tools. For instance the performance trend can be time needed to close a particular valve collected throughout its life time. The performance trend data of the functionality which failure conditions have to be derived can be compared with the performance trends comprised in the reference trend data. This can be done for instance by using Granger causality approach enabling selecting a time series which can be used for forecasting another one. Utilization of the Granger causality approach in this case can enable selecting the performance trend in the reference trend data which can be used for predicting performance of the functionality which failure conditions have to be derived and therefore for derivation of the failure conditions of the functionality specifying conditions when a probability of occurrence of a failure of the functionality in a process of execution of further batches of commands by the electromechanical medical device is above a predefined value.

In a more general way, since interaction between different components in the electromechanical medical tool can be complex, the reference trend data can comprise functionality performance values characterizing performance of functionalities of electromechanical medical devices, wherein the functionalities can be different and/or the electromechanical medical devices can have different device types. The electromechanical devices can be comprised in the set, when collection of the reference data can be limited to the electromechanical medical devices of the set. Alternatively the collection of the reference data can be extended beyond the set. In this case the control system can receive from the exchange server functionality performance values characterizing performance of one or more functionalities of the electromechanical medical device which is not comprised in the set. The exchange server can store the functionality performance values and provide their exchange between different control systems in a similar way as storage and exchange of batches of commands between different control systems is performed.

The memory 145 can stores instructions of a computer executable code which execution by the computer processor 144 causes the control system 140 to perform a control method depicted on FIG. 4. The method depicted on FIG. 4 begins with process block 230. In process block 230 the control system 140 stores in the database 143 the functionality performance value assigned to the performance trend data. The functionality performance value characterizes performance of the functionality which is activated in the process of the execution of the batch of commands by the electromechanical medical device in process block 204. The functionality performance value is comprised in the performance data received by the control system in process block 208. The database is configured to store performance trend data related to the performance of the functionality. Process block 231 is executed after process block 230. Optional process block 231 is executed after process block 230. In process block 231 functionality performance values characterizing performance of one or more functionalities of one or more other electromechanical medical devices are received from the exchange server. The received functionality performance values are comprised in a reference trend data. Process block 231 can be executed by the control system. Process block 232 is executed after process block 231 is the latter is executed, otherwise process block 232 is executed after process block 230. In process block 232 failure conditions of the functionality are derived on a basis of a comparison of the performance trend data with the reference trend data, wherein the failure conditions specify conditions when a probability of occurrence of a failure of the functionality in a process of execution of further batches of commands by the electromechanical medical device is above a predefined value. Process block 232 can be executed by the control system. Process block 233 is executed after process block 232. Process block 233 is the same as process block 220. Process block 233 is not executed when results of execution of process block 220 are already available. Process block 234 is executed after process block 233 is executed after process block 233 if the latter is executed otherwise process block 234 is executed after process block 232. In process block 234 a service application in a list of the service applications stored in the database 143 is identified, wherein in the database each of the service applications in the list is associated with the respective device type of the electromechanical medical device. Process block 234 can be executed by the control system. Process block 235 is executed after process block 234. In process block 235 an alert message is sent to the identified application. The alert message comprises the failure conditions, the identified device type, and the identification information. Process block 235 can be executed by the control system as well. The service application can schedule a maintenance of the electromechanical medical device on a basis of information of the alert message in order to avoid its failure.

The receiving of the performance data in process block 208 can be performed using an input-output port (e.g. 141) of the control system and an input-output port (e.g. 111a) of the electromechanical medical device (e.g. 111). These input-output ports are communicatively coupled with each other, e.g. via the computer network 161. The control system 140 is configured to register a data transmission value characterizing a property of a data carrying signal received by the input-output port of the control system from the input-output port of the electromechanical medical device. For instance the data transmission value can be an amplitude, a frequency, or a slew rate of the data carrying signal. The control system can be configured to register several of them simultaneously. The sending of the performance data comprises a step of the control system registering the data transmission value in a process of the sending of the performance data. The database is configured to store trend data characterizing properties of the data carrying signal. The trend data can indicate degradation of the electromechanical medical device and in particular degradation of its controller. For instance decrease in the amplitude of the data carrying signal can indicate that a power supply or a battery of the electromechanical device is degrading. Changes in frequency of the data carrying signal and/or slew rate can indicate degradation of the I/O port of the electromechanical medical device. The data transmission values can be used for prediction of failures in the same way as the functionality performance values. The exchange server can store and provide exchange of the data transmission values registered in a process of operation of electromechanical medical devices in the same way as it is implemented for the functionality performance values. The data transmission values can be used instead of the functionality performance values for prediction and management of failures in process blocks of the method depicted on FIG. 4.

The preceding figures and accompanying description illustrate the example processes and computer implementable techniques. But example environment (or their software or other components) contemplate using, implementing, or executing any suitable technique for performing these and other tasks. It will be understood that these processes are for illustration purposes only and that the described or similar techniques may be performed at any appropriate time, including concurrently, individually, in parallel, and/or in combination. In addition, many of the operations in these processes may take place simultaneously, concurrently, in parallel, and/or in different orders than as shown. Moreover, the example environment may use processes with additional, fewer and/or different operations, as long as the methods remain appropriate.

In other words, although this disclosure has been described in terms of certain implementations and generally associated methods, alterations and permutations of these implementations and methods will be apparent to those skilled in the art. Accordingly, the above description of example implementations does not define or constrain this disclosure. Other changes, substitutions, and alterations are also possible without departing from the spirit and scope of this disclosure.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example, a programmable processor, a computer, or multiple processors or computers. The apparatus can also be or further include special purpose logic circuitry, e.g., a central processing unit (CPU), a FPGA (field programmable gate array), or an ASIC (application specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a FPGA, or an ASIC.

Computers suitable for the execution of a computer program can be based on general or special purpose microprocessors, both, or any other kind of CPU. Generally, a CPU will receive instructions and data from a read only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically-erasable programmable read-only memory (EEPROM), and flash memory devices; magnetic disks, e.g., internal hard disks or removable disks; magneto optical disks; and CD ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back end component, e.g., as a data server, or that includes a middleware component, e.g., an application server, or that includes a front-end component, e.g., a client computer having a graphical user interface or a web browser through which a user can interact with an implementation of the subject matter described in this specification, or any combination of one or more such back end, middleware, or front end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any implementation or on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some causes be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

The invention claimed is:

1. A control method for controlling a set of electromechanical medical devices, the method comprising:
   receiving, by a control system, an instruction to be executed by an electromechanical medical device of the set;
   translating the received instruction into a batch of commands parsable by an electronic controller of the electromechanical medical device;
   sending the batch of commands from the control system to the electromechanical medical device;
   receiving the batch of commands by the electromechanical medical device;
   causing, by the electronic controller, the electromechanical medical device to execute the batch of commands;
   registering, by the electronic controller, performance data related to the execution of the batch of commands;
   sending the performance data from the electromechanical medical device to the control system;
   receiving the performance data by the control system using an input-output port of the control system and an input-output port of the electromechanical medical device, the input-output ports being communicatively coupled with each other via a computer network,
   registering, by the control system, a data transmission value characterizing an amplitude, a frequency, or a slew rate of a data carrying signal received by the input-output port of the control system from the input-output port of the electromechanical medical device, the receiving of the performance data comprises registering, by the control system, the data transmission value in a process of the receiving of the performance data;
   storing, in a database of the control system, the data transmission value assigned to trend data, the trend data characterizing the amplitude, the frequency, or the slew rate of the data carrying signal; and
   deriving failure conditions of the electromechanical medical device based on the trend data and reference trend data, the failure conditions specifying conditions when a probability of occurrence of a failure of the electromechanical medical device in a process of execution of further batches of commands by the electromechanical medical device is above a desired value.

2. The control method of claim 1,
   wherein the instruction comprises an instruction specification and an identification information for identifying the electromechanical medical device,
   wherein the control method further comprises:
      storing, in a database of the control system, batches of commands parsable by electronic controllers of the electromechanical medical devices of the set, technical data enabling identification of a device type of electromechanical medical device by respective identification information of the electromechanical medical device, and parameter values for entering in parameter fields of commands of the batches of commands, each of the electromechanical medical devices of the set having a respective device type, each of the batches of commands being associated with a respective instruction specification and a respective device type of an electromechanical medical device of the set, each of the parameter values being associated with a respective command in the batch of commands and an identification information of a respective electromechanical medical device of the set, and
   wherein the translating of the received instruction into the batch of commands parsable by the electronic controller of the electromechanical medical device comprises:
      identifying, in the database, a device type associated with the identification information comprised in the instruction using the technical data;

identifying, in the database, the batch of commands associated with the identified device type and the instruction specification comprised in the instruction;

identifying, in the database, a parameter value associated with the identification specification and a command of the identified batch of commands; and entering the identified parameter value in a respective parameter field of the command of the identified batch of commands.

3. The control method of claim 1, wherein the performance data comprises an indicator value, and wherein the control method further comprises:

receiving, by the control system, another instruction to be executed by the electromechanical medical device of the set;

translating the another received instruction into another batch of commands parsable by the electronic controller of the electromechanical medical device; and performing the following in response to the indicator value comprised in the performance data received by the control system complying with a specification of the indicator value, compliance of the indicator value with the specification of the indicator value indicating that the batch of commands is executed successfully on the electromechanical medical device;

sending the another batch of commands from the control system to the electromechanical medical device;

receiving the another batch of commands by the electromechanical medical device;

the electronic controller causing the electromechanical medical device to execute the another batch of commands;

registering, by the electronic controller, another performance data related to the execution of the another batch of commands;

sending the another performance data from the electromechanical medical device to the control system; and receiving, by the control system, the another performance data.

4. The control method of claim 1, further comprising:

storing, in a database of the control system, rules determining sequence of execution of batches of commands;

receiving, by the control system, another instruction to be executed by another electromechanical medical device of the set;

translating the another received instruction into another batch of commands parsable by another electronic controller of the another electromechanical medical device;

sending the another batch of commands from the control system to the another electromechanical medical device, wherein the sending of the another batch of commands from the control system to the another electromechanical medical device is executed after the receiving of the performance data by the control system in response to one of the rules indicating the batch of commands has to be executed before the another batch of commands;

receiving the another batch of commands by the another electromechanical medical device; and the another electronic controller causing the another electromechanical medical device to execute the another batch of commands.

5. The control method of claim 1, comprising:

reporting, by the control system, a failure of the electromechanical medical device in response to a value of a time interval between the sending of the batch of commands from the control system to the electromechanical medical device and the receiving of the performance data by the control system being bigger than a desired value.

6. The control method of claim 1, wherein the instruction comprises an instruction specification and an identification information for identifying the electromechanical medical device, and the control method comprises:

storing, in a database of the control system, batches of commands parsable by electronic controllers of the electromechanical medical devices of the set and technical data enabling identification of a device type of the electromechanical medical device by the identification information of the electromechanical medical device, each batch of commands stored in the database being associated with a respective instruction specification and a respective device type of an electromechanical medical device of the set, each electromechanical medical device having a respective device type;

storing, in an exchange server communicatively coupled to the control system, batches of commands parsable by electronic controllers of electromechanical medical devices, instruction specifications, and values of time interval, each batch of commands stored on the exchange server associated with a respective device type, a respective instruction specification, and respective value of time interval;

identifying, in the database, a device type associated with the identification information comprised in the instruction using the technical data;

identifying, in the database, the batch of commands associated with the identified device type and the instruction specification comprised in the instruction, wherein the identified batch of commands is the one which is executed in the step of the electronic controller causing the electromechanical medical device to execute the batch of commands;

sending, by the control system, to the exchange server the identified device type, the instruction specification comprised in the instruction, the identified batch of commands, the desired value, and the value of the time interval between the sending of the batch of commands from the control system to the electromechanical medical device and the receiving of the performance data by the control system;

storing, in the exchange server, the identified batch of commands in association with the identified device type, the instruction specification comprised in the instruction, and the value of the time interval between the sending of the batch of commands from the control system to the electromechanical medical device and the receiving of the performance data by the control system; and receiving, by the control system, from the exchange server, the batch of commands stored on the exchange server in response to the value of the time interval between the sending of the batch of commands from the control system to the electromechanical medical device and the receiving of the performance data by the control system being bigger than the desired value and the batch of commands stored on the exchange server being associated with the identified device type, the instruction specification included in the instruction, and the value of time interval being equal or less than the value of the time interval between the sending of the batch of commands from the control system to the electromechanical medical device and the receiving of the performance data by the control system.

7. The control method of claim 1,
wherein the performance data comprises a functionality performance value characterizing performance of a functionality of the electromechanical medical device, wherein the control method comprises:
registering the functionality performance value in response to the functionality being activated in a process of the execution of the batch of commands by the electromechanical medical device
reporting, by the control system, a failure of the functionality in response to the functionality performance value does not comply with a specification of the functionality performance value.

8. The control method of claim 1,
wherein the instruction comprises an instruction specification and an identification information for identifying the electromechanical medical device, and
wherein the control method comprises:
registering, a functionality performance value in response to a functionality being activated in a process of execution of the batch of commands by the electromechanical medical device, each electromechanical medical device having a respective device type, the performance data comprising the functionality performance value characterizing performance of the functionality of the electromechanical medical device,
storing, in a database of the control system, batches of commands parsable by electronic controllers of electromechanical medical devices of the set and technical data enabling identification of the device type of the electromechanical medical device by an identification information of the electromechanical medical device, each of the batches of commands stored in the database associated with a respective instruction specification and a respective device type of an electromechanical medical device of the set;
storing, in an exchange server communicatively coupled to the control system, batches of commands parsable by electronic controllers of electromechanical medical devices, instruction specifications, and functionality performance values characterizing performance of functionalities of electromechanical medical devices, each of the batches of commands stored on the exchange server associated with a respective device type, a respective instruction specification, and at least one respective functionality performance value;
identifying, in the database, a device type associated with the identification information comprised in the instruction using the technical data;
identifying, in the database, the batch of commands associated with the identified device type and the instruction specification description comprised in the instruction, wherein the identified batch of commands is the one which is executed in the step of the electronic controller causing the electromechanical device to execute the batch of commands;
sending, by the control system, to the exchange server the identified device type, the instruction specification comprised in the instruction, the identified batch of commands, the specification, and the functionality performance value characterizing performance of the functionality which is activated in the process of the execution of the batch of commands by the electromechanical medical device;
storing, by the exchange server, the identified batch of commands in association with the identified device type, the instruction specification comprised in the instruction, and the functionality performance value characterizing performance of the functionality which is activated in the process of the execution of the batch of commands by the electromechanical medical device; and
receiving, by the control system, from the exchange server the batch of commands stored on the exchange server in response to the functionality performance value characterizing performance of the functionality which is activated in the process of the execution of the batch of commands by the electromechanical medical device not complying with the specification and the batch of commands stored on the exchange server being associated with the identified device type, the instruction specification included in the instruction and the functionality performance value complying with the specification.

9. The control method of claim 1, wherein
the instruction comprises an identification information for identifying the electromechanical medical device, and
the control method comprises:
storing, in the database, a list of service applications and technical data enabling identification of a device type of the electromechanical medical device by respective identification information of the electromechanical medical device, in the database each of the service applications in the list is associated with a respective device type of the electromechanical medical device, each of the electromechanical medical devices of the set having a respective device type,
identifying in the database a device type associated with the identification information comprised in the instruction using the technical data;
identifying a service application in the list, wherein the identified service application is associated with the identified device type; and
sending an alert message to the identified application, the alert message comprising the failure conditions, the identified device type, and the identification information.

10. The control method of claim 1, wherein the reference trend data comprises functionality performance values characterizing performance of one or more functionalities of one or more other electromechanical medical devices.

11. The control method of claim 9, wherein at least one of one or more electromechanical medical devices is not included in the set, wherein the control method further comprises:
receiving, by the control system, from an exchange server, functionality performance values characterizing performance of one or more functionalities of the at least one of the one or more electromechanical medical devices.

12. The control method of claim 9, wherein one or more other electromechanical medical devices are comprised in the set.

13. The control method of claim 1, further comprising:
registering a functionality performance value in response to a functionality being activated in a process of the execution of the batch of commands by the electromechanical medical device, the performance data including the functionality performance value characterizing performance of the functionality of the electromechanical medical device; and reporting, by the control system, a failure of the functionality in response to the functionality performance value not complying with a specification of the functionality performance value.

14. The control method of claim 1, wherein the reference trend data comprises functionality performance values characterizing performance of one or more functionalities of one or more other electromechanical medical devices.

15. The control method of claim 1, wherein the instruction comprises an identification information for identifying the electromechanical medical device, and wherein the control method comprises:

storing, in the database, a list of service applications and technical data enabling identification of a device type of the electromechanical medical device by respective identification information of the electromechanical medical device, in the database each of the service applications in the list is associated with a respective device type of the electromechanical medical device, each of the electromechanical medical devices of the set having a respective device type;

identifying in the database a device type associated with the identification information comprised in the instruction using the technical data;

identifying a service application in the list, wherein the identified service application is associated with the identified device type; and sending an alert message to the identified application, the alert message comprising the failure conditions, the identified device type, and the identification information.

16. A non-transitory computer readable medium storing computer instructions stored therein which when executed by a computer processor controlling a control system cause the computer processor to perform the control method of claim 1.

17. A control system for controlling a set of electromechanical medical devices, wherein the control system comprises a computer processor and a non-transitory computer memory storing instructions of a computer executable code which execution by the computer processor causes the control system to perform the following:

receiving an instruction to be executed by an electromechanical medical device of the set;

translating the received instruction into a batch of commands parsable by an electronic controller of the electromechanical medical device;

sending the batch of commands to the electromechanical medical device;

receiving, by the control system, performance data related to the execution of the batch of commands, the receiving of the performance data is performed using an input-output port of the control system and an input-output port of the electromechanical medical device, the input-output port of the control system and the input-output port of the electromechanical medical device being communicatively coupled with each other via a computer network, the receiving of the performance data comprises a step of the control system registering a data transmission value in a process of the receiving of the performance data, the data transmission value characterizing an amplitude, a frequency, or a slew rate of a data carrying signal received by the input-output port of the control system from the input-output port of the electromechanical medical device;

storing, in a database of the control system, trend data characterizing the amplitude, the frequency, or the slew rate of the data carrying signal;

storing, in the database, the data transmission value assigned to the trend data; and deriving failure conditions of the electromechanical medical device on a basis of comparison of the trend data with reference trend data, the failure conditions specifying conditions when a probability of occurrence of a failure of the electromechanical medical device in a process of execution of further batches of commands by the electromechanical medical device is above a desired value.

* * * * *